United States Patent
Naef et al.

(10) Patent No.: US 7,321,067 B2
(45) Date of Patent: Jan. 22, 2008

(54) PROCESS FOR THE PREPARATION OF 1,4-DIALKYL-2,3-DIOL-1,4-BUTANEDIONE

(75) Inventors: Ferdinand Naef, Seewen (CH); René Decorzant, Onex (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/692,839

(22) Filed: Mar. 28, 2007

(65) Prior Publication Data

US 2007/0167656 A1    Jul. 19, 2007

Related U.S. Application Data

(63) Continuation of application No. PCT/IB2005/053511, filed on Oct. 27, 2005.

(30) Foreign Application Priority Data

Nov. 2, 2004   (WO) ................. PCT/IB2004/003631

(51) Int. Cl.
*C07C 45/72*   (2006.01)
(52) U.S. Cl. ..................... 568/390; 568/392
(58) Field of Classification Search ................ None
See application file for complete search history.

(56) References Cited

U.S. PATENT DOCUMENTS 4,234,518 A    11/1980  Yoshida et al. ............. 568/377

FOREIGN PATENT DOCUMENTS

CH    474 465    8/1969

OTHER PUBLICATIONS

George Buchi et al., "Syntheses of 2,5-Dimethyl-4-hydroxy-2,3-dihydrofuran-3-one (Furaneol), a Flavor Principle of Pineapple and Strawberry", J. Org. Chem., vol. 38, No. 1, pp. 123-125 (1978).
Luciano Bassignani et al., "Novel Applications of the Potassium Chlorate Osmium Tetroxide Oxidizing System. Synthesis of α-Diearbonyl Derivatives from Acetylenic Compounds. Synthesis of a 2,3-Dihydroxy-1,4-dione from a 2,5-Dialkylfuran", J. Org, Chem., vol. 43, No. 21, pp. 4245-4247 (1978).
Mark A. Briggs et al., "Synthesis of 4-Hydroxy-2,5-dimethylfuran-3(2H)-one (Furaneol) from (2R,3R)-tartaric Acid", Journal of Chem. Soc. Perkin Trans. 1, pp. 795-798 (1985).
A.M.B.S.R.C.S. Costa et al., "Lithiationin Flavones, Chromones, Coumarins, and Venzofuran Derivatives", , J. Chem. Soc. Perkin Trans 1, pp. 799 (1985).

*Primary Examiner*—Sikarl A. Witherspoon
(74) *Attorney, Agent, or Firm*—Winston & Strawn LLP

(57) ABSTRACT

The present invention relates to a process for the preparation of compounds of a 1,4-dialkyl-2,3-diol-1,4-butanedione by a catalytic aldol condensation between an alkyl glyoxal and an α-hydroxy ketone.

7 Claims, No Drawings

PROCESS FOR THE PREPARATION OF 1,4-DIALKYL-2,3-DIOL-1,4-BUTANEDIONE

CROSS-REFERENCE TO RELATED APPLICATIONS

This application is a continuation of International application PCT/IB2005/053511 filed Oct. 27, 2005, the entire content of which is expressly incorporated herein by reference thereto.

TECHNICAL FIELD

The present invention relates to the field of organic synthesis and more particularly to a new process for the preparation of 1,4-dione-2,3-diols as defined further below.

BACKGROUND

The compounds of formula (I), as defined below, can be useful as starting material for the construction compounds having a more complex skeletons, such as 4-hydroxy-2,5-dimethyl-3(2H)-furanone (known as Furaneol®, Trademark of Firmenich SA).

Various processes for the preparation of compounds of formula (I) have been reported, for example Briggs et al, J. Chem. Soc. Perkin. Trans. I, 1985, 795 relates to a multistep synthesis of the 3,4-dihydroxyhexane-2,5-dione starting from the tartaric acid, or Bassignani et al, J. Org. Chem., 1978, 43, 4245 relates to the synthesis of the 3,4-dihydroxyhexane-2,5-dione by oxidizing the expensive 2,5-dimethylfuran with the toxic and expensive $KClO_3/OsO_4$ system. Another reported method to synthesize compounds (I) is the reductive dimerisation of glyoxals promoted by various methods (for instance see EP 368211 or Büchi et al, J. Org. Chem., 1973, 38, 123).

The above-mentioned methods of preparation are in general quite long and expensive or imply the use of a large excess of heavy metal which implies problems of purification of the final product and of waste treatment.

To the best of our knowledge, in the prior art there is no report of an aldol condensation giving a direct access to compounds of formula (I).

SUMMARY OF THE INVENTION

The present invention now relates to the field of organic synthesis and more particularly to a process for the preparation of compounds of formula (I) by the aldol condensation between an alkyl glyoxal (II) and an acetol derivative (III), said condensation being promoted a catalyst, according to Scheme (1):

Scheme 1:
Aldol condensation of glyoxals and acetols according to the invention

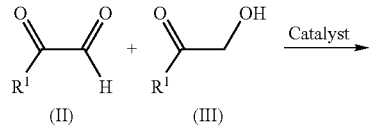

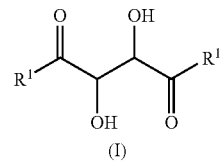

wherein $R^1$ represents a linear or branched $C_1$ to $C_5$ alkyl group.

DETAILED DESCRIPTION OF THE INVENTION

In order to overcome the problems aforementioned, and provide also an alternative process for the preparation of compounds (I), the present invention relates to a catalytic process aimed at the synthesis of compounds (I) in a single step and with good yields.

The process of the invention concerns more specifically the aldol condensation between an alkyl glyoxal (II) and an acetol derivative (III). Indeed, we have now surprisingly discovered that a specific type of catalyst is able to promote the invention reaction.

Therefore, the process of the invention concerns the preparation of a compound of formula

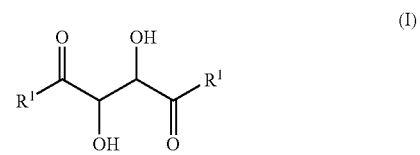

wherein $R^1$ represents a linear or branched $C_1$ to $C_5$ alkyl radical, said process being characterized in that it comprises the aldol condensation, in a water-containing reaction medium, between a glyoxal of formula

wherein $R^1$ has the same meaning as defined above, and an α-hydroxy ketone of formula

wherein $R^1$ has the same meaning as defined above, in the presence of catalyst of formula $FeX_3$ or $MX_2$, wherein M is $Zn^{2+}$, $Mg^{2+}$, $Cu^{2+}$, $Fe^{2+}$ or $Ca^{2+}$ and X is a $C_1$-$C_7$ carboxylate, an halide or an acetylacetonate derivative of formula (R²COCHCOR²)⁻, R² representing a $C_1$-$C_3$ alkyl group or a phenyl group.

According to a particular embodiment of the invention, $R^1$ represents a methyl group and therefore the glyoxal (II) is methyl glyoxal, the acetol (III) is acetol (i.e. 1-hydroxy-2-propanone) and the dihydroxy-dione (I) is 3,4-dihydroxyhexane-2,5-dione.

As mentioned above, the reaction is carried out in a water-containing reaction medium. By "water-containing reaction medium" it is meant here the medium wherein the reaction takes place, said medium containing at least 10% of water, percentage being relative to its own weight. In general the reaction medium comprises also an organic solvent, which can be water miscible or not. In general, any solvent which is inert under the experimental conditions is useful. In a particular embodiment of the invention, such a solvent is an ether or an ester such as tetrahydrofurane (THF), methyl-tert-butyl ether (MTBE) or ethylacetate.

As the process of the invention takes place in a water-containing reaction medium the pH of the solution has great importance for the course of the reaction. In that respect, we have discovered that, in order to ensure higher yields of compound (I), it is more advantageous to perform the invention's process in a weakly acidic to neutral medium.

According to an embodiment of the invention the present process is preferably carried out in a reaction medium having a pH of between 3.5 and 7, preferably between 4 and 6.5.

According to a particular embodiment of the invention the catalysts are the ones of formula $MX_2$, wherein M is $Zn^{2+}$ or $Mg^{2+}$, and X is an acetate, propionate, fluoride or acac, i.e., $(CH_3COCHCOCH_3)^-$. In particular, and as non-limiting examples of suitable catalyst, one can cite in particular $Zn(acetate)_2$, $Zn(acac)_2$, $ZnF_2$ or $Mg(acac)_2$.

According to a further embodiment of the invention one may cite as catalysts $ZnX_2$, wherein X represents a $C_1$-$C_3$ carboxylate, such as $Zn(acetate)_2$.

The amount in which the catalyst may be employed in the invention's process is typically comprised between 0.01 and 20 molar %, relative to the glyoxal. In a preferred embodiment of the process of the invention the catalyst is used in a concentration comprised between about 0.02 and 15 molar %.

The amount in which the acetol derivative (III) may be employed in the invention's process is typically comprised between 50 and 250 molar %, relative to the glyoxal.

The temperature at which the process of the invention can be carried out is comprised between 0° C. and 100° C., more preferably between 20° C. and 60° C.

EXAMPLES

The invention will now be described in further detail by way of the following example, wherein the temperatures are indicated in degrees centigrade and the abbreviations have the usual meaning in the art.

Example 1

Experimental Procedure

A solution of methyl glyoxal 40% wt in water (9 g, 50 mmoles), zinc acetate (0.44 g) and hydroxy-acetone (7.4 g) in ethyl acetate (20 ml) were stirred during 40 h at 38/40° (pH of the reaction medium was around 4.5). At the end of the reaction (which can be checked by gas chromatography), the reaction mixture was extracted with ethyl acetate (3×50 ml). The organic phase was washed to neutral with brine (1×), dried over magnesium sulphate and concentrated under vacuum giving 6 g of the crude 3,4-dihydroxyhexane-2,5-dione who was Bulb-to-bulb distilled at 0.1 mbar and 120-150° to obtain 3.8 g of a mixture of the two 3,4-dihydroxyhexane-2,5-dione isomers.

The product obtained had the same ¹H-NMR spectra as those described in Büchi et al, J. Org. Chem., 1973, 38, 123.

Following the same experimental procedure as above several other experiments according to the invention were performed. The results are summarized in the Table 1.

TABLE 1

Aldol condensation between methyl glyoxal and acetol to provide 3,4-dihydroxyhexane-2,5-dione, threo and meso isomers (2:1)

| N° | Glyoxal (mmol.) | Acetol (m.e.)[1] | Solvent (ml) | pH | T (° C.) | Time (h) | Catalyst (m.e.)[1] | yield |
|---|---|---|---|---|---|---|---|---|
| 1 | 50 | 5 | THF (20) | 7.0 | 20° | 60 | Zn(acac)₂ (0.08) | 20% |
| 2 | 50 | 2.5 | H₂O (20) | 5.8 | 20° | 72 | Zn(acac)₂ (0.08) | 20% |
| 3 | 50 | 2 | EtOAc (20) | 4.7 | 20° | 168 | Zn(acetate)₂ (0.04) | 42% |
| 4 | 50 | 2 | EtOAc (20) | 4.5 | 40° | 40 | Zn(acetate)₂ (0.04) | 32% |
| 5 | 50 | 2 | EtOAc (20) | 4.5 | 40° | 9 | Zn(acetate)₂ (0.10) | 30% |
| 6 | 50 | 5 | EtOAc (20) | 2.6 | 40° | 24 | Zn(acetate)₂ (0.10) | 22% |
| 7 | 50 | 2 | EtOAc (20) | 4.7 | 20° | 168 | ZnF₂ (0.04) | 25% |
| 8 | 50 | 2 | EtOAc (20) | 5.5 | 20° | 168 | Mg(acetate)₂ (0.04) | 18% |
| 9 | 50 | 2 | EtOAc (20) |  | 20° | 216 | Mg(acac)₂ (0.04) | 23% | m.e. = molar equivalent;
[1]relative to methyl glyoxal

What is claimed is:

1. A process for the preparation of a compound of formula

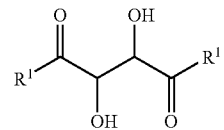

(I)

wherein $R^1$ represents a linear or branched $C_1$ to $C_5$ alkyl radical, the process comprising performing an aldol condensation, in a water-containing reaction medium, between a glyoxal of formula

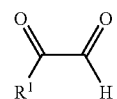

(II)

wherein $R^1$ has the same meaning as defined above, and an α-hydroxy ketone of formula

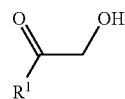

(III)

wherein $R^1$ has the same meaning as defined above,
in the presence of catalyst of formula $FeX_3$ or $MX_2$, wherein M is $Zn^{2+}$, $Mg^{2+}$, $Cu^{2+}$, $Fe^{2+}$ or $Ca^{2+}$ and X is a $C_1$-$C_7$ carboxylate, an halide or a acetylacetonate derivative of formula $(R^2COCHCOR^2)^-$, with $R^2$ representing a $C_1$-$C_3$ alkyl group or a phenyl group.

2. The process according to claim 1, wherein $R^1$ represents a methyl group.

3. The process according to claim 1, wherein the water-containing reaction medium contains at least 10% of water, percentage being relative to its own weight.

4. The process according to claim 3, wherein the reaction medium has a pH of between 3.5 and 7.

5. The process according to claim 1, wherein the catalyst is of formula $MX_2$, wherein M is $Zn^{2+}$ or $Mg^{2+}$, and X is an acetate, propionate, fluoride or $(CH_3COCHCOCH_3)^-$.

6. The process according to claim 5, wherein the catalyst is $Zn(acetate)_2$, $Zn(acac)_2$, $ZnF_2$ or $Mg(acac)_2$.

7. The process according to claim 1, wherein the catalyst is $ZnX_2$, wherein X represents a $C_1$-$C_3$ carboxylate.

* * * * *